(12) United States Patent
Dobboletta

(10) Patent No.: US 10,137,178 B2
(45) Date of Patent: Nov. 27, 2018

(54) DENTAL GEL COMPOSITION OF PAPAIN FOR THE ATRAUMATIC TREATMENT OF CARIES AND METHOD OF PREPARING SAME

(71) Applicant: BRIX USA, LLC, Newark, DE (US)

(72) Inventor: Mauricio Dobboletta, Santa Fe (AR)

(73) Assignee: BRIX USA, LLC, Newark, DE (US)

( * ) Notice: Subject to any disclaimer, the term of this patent is extended or adjusted under 35 U.S.C. 154(b) by 0 days.

(21) Appl. No.: 15/312,431

(22) PCT Filed: May 20, 2015

(86) PCT No.: PCT/US2015/031669
§ 371 (c)(1),
(2) Date: Nov. 18, 2016

(87) PCT Pub. No.: WO2015/179463
PCT Pub. Date: Nov. 26, 2015

(65) Prior Publication Data
US 2017/0100464 A1   Apr. 13, 2017

(30) Foreign Application Priority Data

May 20, 2014   (AR) ............................. P20140101998

(51) Int. Cl.
| | |
|---|---|
| *A61Q 11/00* | (2006.01) |
| *A61K 38/48* | (2006.01) |
| *A61K 8/66* | (2006.01) |
| *A61K 8/04* | (2006.01) |
| *A61C 19/06* | (2006.01) |
| *A61K 9/06* | (2006.01) |
| *A61K 47/02* | (2006.01) |
| *A61K 47/10* | (2017.01) |
| *A61K 47/14* | (2017.01) |
| *A61K 47/18* | (2017.01) |
| *A61K 47/22* | (2006.01) |
| *A61K 47/26* | (2006.01) |
| *A61K 47/36* | (2006.01) |
| *A61K 8/24* | (2006.01) |
| *A61K 8/34* | (2006.01) |
| *A61K 8/37* | (2006.01) |
| *A61K 8/41* | (2006.01) |
| *A61K 8/49* | (2006.01) |
| *A61K 8/86* | (2006.01) |
| *A61K 8/11* | (2006.01) |
| *A61C 5/62* | (2017.01) |

(52) U.S. Cl.
CPC ............ *A61K 38/4873* (2013.01); *A61C 5/62* (2017.02); *A61C 19/063* (2013.01); *A61K 8/042* (2013.01); *A61K 8/11* (2013.01); *A61K 8/24* (2013.01); *A61K 8/345* (2013.01); *A61K 8/37* (2013.01); *A61K 8/41* (2013.01); *A61K 8/49* (2013.01); *A61K 8/66* (2013.01); *A61K 8/86* (2013.01); *A61K 9/06* (2013.01); *A61K 47/02* (2013.01); *A61K 47/10* (2013.01); *A61K 47/14* (2013.01); *A61K 47/18* (2013.01); *A61K 47/22* (2013.01); *A61K 47/26* (2013.01); *A61K 47/36* (2013.01); *A61Q 11/00* (2013.01); *C12Y 304/22002* (2013.01)

(58) Field of Classification Search
None
See application file for complete search history.

(56) References Cited

U.S. PATENT DOCUMENTS

| | | | | |
|---|---|---|---|---|
| 2,689,170 | A * | 9/1954 | King ................... | A61K 8/44 424/54 |
| 3,228,844 | A * | 1/1966 | Lyon ................... | A61K 8/673 424/48 |
| 4,986,981 | A * | 1/1991 | Glace ................... | A61K 8/26 424/49 |
| 6,331,291 | B1* | 12/2001 | Glace ................... | A61K 8/732 424/49 |
| 2007/0275045 | A1 | 11/2007 | Evans et al. | |
| 2008/0193390 | A1* | 8/2008 | Boucas ............... | A61K 8/466 424/50 |
| 2008/0206377 | A1* | 8/2008 | Scott ................... | A61K 36/00 424/777 |
| 2009/0068255 | A1 | 3/2009 | Yu et al. | |

FOREIGN PATENT DOCUMENTS

| | | | |
|---|---|---|---|
| AR | | 085779 A1 | 10/2013 |
| WO | WO 2005020946 A1 | | 10/2013 |
| WO | WO 2014016644 A1 | | 1/2014 |

OTHER PUBLICATIONS

SK Bussadori, LC Castro, AC Galvao. "Papain Gel: A New Chemo-Mechanical Caries Removal Agent." The Journal of Clinical Pediatric Dentistry, vol. 30 No. 2, 2005, pp. 115-119. (Year: 2005).*

* cited by examiner

*Primary Examiner* — Isaac Shomer
(74) *Attorney, Agent, or Firm* — Osha Liang LLP

(57) ABSTRACT

A papain dental gel composition is disclosed for the atraumatic treatment of caries which comprises papain with a final activity of at least 3,000 U/mg, wherein the papain is bio-encapsulated in a mixture of pH=7 buffer-$C_{3-6}$ polyol-pectin-$C_{2-6}$ alkanolamine-nonionic emulsifier, together with pharmaceutically acceptable coloring agents, preservatives and solvents. A method of preparing said papain composition is also disclosed.

24 Claims, 10 Drawing Sheets

DENTAL GEL COMPOSITION OF PAPAIN FOR THE ATRAUMATIC TREATMENT OF CARIES AND METHOD OF PREPARING SAME

FIELD OF THE INVENTION

The present invention is related to the atraumatic treatment of caries, particularly with a chemical composition for manual use for the softening of the decayed dentine in teeth.

PRIOR ART BACKGROUND

According to the World Health Organization (WHO), 90% of the population suffers from dental caries and 80% prefers not to go to the dentist's office since they are afraid of local anesthesia and the sound produced by the turbine (drill), while describing the technique as negative and with a high degree of rejection, as they consider noise, vibration and pressure as obstacles to a comprehensive dental rehabilitation.

The technique of manual removal of the caries tissue appears as an alternative which offers greater comfort to patients of all ages. After carrying out some research on literature and clinical cases related to this issue, the action of a specific enzyme which synergistically works in the selective manual removal of the caries tissue is surprising, thus enhancing the technique and making it more amenable both for the patient and the dentist.

From the 70's on, several researchers have suggested different composition formulas for the removal of the dental caries, based on the principle of maximum preservation of the healthy dental structure.

In 1975, Habib et al. (Habib C. M., Kronman J., Goldman M., A chemical evaluation of collagen and hydroxyproline alter treatment with GK-101(N-chloroglycine). Pharmacol. Ther. Dent., v.2, 209-215, 1975) started this methodology by using 5% sodium hypochlorite having a non-specific proteolytic effect which removed the decayed dental tissue. However, it was a toxic, irritant agent for the mouth tissues and, for this reason, a solution was proposed which involved addition of glycine, sodium chloride and sodium hydroxide to the 5% sodium hypochlorite with the purpose of solving such inconvenience. The modified formula became known as GK-101 and consisted of N-monochloroglycine (Goldman M., Kronman J. H.; A preliminary report on a chemomechanical means of removing caries. J. Am. Dent. Assoc. 1976; 93(6):1149-53). Even though this made the process much more effective than hypochlorite alone, it was slower to remove the caries tissue. Furthermore, this process did not include adhesive dental materials to perform fillings, and therefore the use of turbines was still necessary to shape the cavities.

To the N-monochloroglycine comprising formula, aminobutyric acid was added, thus obtaining a composition marketed under the name Caridex (Schutzbank S. G., Galaini J., Kronman J. H., Goldman M., Clarke R. E. A. A Comparative in vitro study of the effect of GK-101 and GK 101E in caries removal. J. Dent. Res. 1978; 57:861-864). Even when it is more effective in disrupting the dentin collagen of the caries, Caridex had some clinical restrictions, among which we could mention: it had higher cost, it required a large vessel with a pump, it required large quantities of solution, it presented several problems during heating and it had a short shelf-life (Beeley J. A., Yip H. K., Stevenson A. G. Chemomechanical caries removal: a review of the techniques and latest developments. Br. Dent. J. 2000; 188:427-430).

In order to render it more effective and easier to handle, this Caridex gel evolved into the Carisolv system, which comprised two agents: a carboxymethylcellulose-based gel with a solution of three different amino acids: lysine, leucine and glutamic acid; the second component is a 0.5% sodium hypochlorite solution. Despite the advantages which were achieved, as are preservation of the healthy dental tissue and reduced use of rotating tools (Ericson D., Zimmerman M., Raber H., Gotrik B., Bornstein R., Thorell J.; Clinical evaluation of efficacy and safety of a new method for chemo-mechanical removal of caries. Caries Res. 1999; 33:171-177), the use of Carisolv could not be systematized, thus limiting its application to a small part of the population due to difficulties of usage such as the need for intensive training and professional records and the need for specific tools, which increased the cost of this solution.

With the aim to globalize the use of this chemical-mechanical system for removal of the dental caries, a gel-type product was launched to the market in 2003, which main component is papain, an enzyme obtained from the *papaya*, similar to human pepsin.

It was created in Brazil by two researchers, Dr. Sandra Kalil Bussadori, Pediatric Dentistry, Professor at Universities of Sao Paulo and Metropolitana de Santos and Dr. Márcia Bouças Miziara, from the pharmaceutical firm Fórmula & Ação Farmácia, and it was given the commercial name Papacarie.

Papacarie comprises papain as the active ingredient, chloramine T, carboxymethylcellulose, sodium chloride, methylparaben, sodium hydroxide, colorings and enough quantity of distilled water to complete the formulation (WO2005020946A1), which was improved later on with a gel composed by papain, chloramine T, pectin, polyethylene glycol, propylene glycol and coloring agents. (WO2014016644A1)

Papain is extracted from the latex of the leaves and fruits of the green adult *papaya, Carica Papaya*, which is grown in tropical countries such as Brazil, India, Ceylon, South Africa and Hawaii.

It is a proteolytic enzyme having bactericide, bacteriostatic and anti-inflammatory properties, working exclusively on the dental dead tissue since it does not contain plasmatic antiprotease $\alpha_1$-antitrypsin which inhibits the proteolytic action of the papain. Because of this, softening of the dead tissue occurs, thus debriding the collagen fibers which are partially degraded, while preserving the healthy tissue as it is not demineralized and it does not have any exposed collagen fibers.

Another component used in the Papacarie formulation is chloramine. It is composed by chlorine and ammonium which have bactericide and disinfectant properties used for the root canal irrigation. It is an additional chemical softener of the decayed dentin, so that the secondary and/or quaternary structure of the collagen is affected because hydrogen bonds are broken, which makes removal of the decayed tissue easier. When checking the effect of the chloramine by using scanning electron microscopy and Vickers microhardness, it was observed that the use of chloramine resulted in open dentinal tubules in the outer layer of the decayed dentin.

Chloramine is a component which is generally hazardous for human health. A few minutes after chloramine intake a person can suffer from sickness, cyanosis, circulatory collapse, foaming at the mouth and respiratory failure.

Chloramine in water containers has caused methemoglobinemia and hemolysis in patients undergoing dialysis. It has also caused bronchospasm when inhaled.

Due to each of its components, Papacarie achieves a synergistic action which makes removal of the caries easier with highly antimicrobial properties and without using special dental tools.

Its major advantages are that it requires less manual pressure, causes less tiredness to the intervening professional and less sensitivity on the patient's behalf.

This gel is especially recommended for the following situations: asymptomatic deep carious lesions reducing the risk of pulp exposure in toddlers, children, adolescents and/or phobic adults or patients with special needs; removal of root caries; chemo-mechanical treatment of the root surface in periodontology, rendering removal of dental calculus or tartar and root isolation easier; and use in public health due to its affordable cost.

No contraindications are mentioned. Innumerable studies have shown that there is no irritation due to direct contact of the gel with the oral tissues. However, there are certain circumstances under which Papacarie should not be applied: when there are symptoms consistent with chronic infectious processes such as fistulas, spontaneous pain or pain on percussion, in patients with systemic diseases which may alter the host's immune response such as diabetes, blood dyscrasias, etc.

This product must be kept under proper cooling and must be removed from the refrigerator fifteen minutes before use in order to apply it at room temperature.

Another gel based on papain and pectin is described in Patent Application AR Number P20120101629, published as AR085779A1. Claim 1 of this document is directed to a chemical-dental formulation which removes the carious tissue, to a manufacturing process and mode of application of same for dental caries or carious tissue removal; characterized by comprising: between 2 and 6% of a proteolytic enzyme, preferably 30,000 U/mg papain; between 0.2 and 1% of an antifungal, preferably Chloramine T; between 0.1 and 0.3% of an antimicrobial coloring agent, preferably Toluidine blue; all the aforementioned components supported by a stabilizing agent, preferably citrus pectin, from 3 to 6% in deionized water, and adjustment to pH 5/7 with a dilute triethanolamine solution in deionized water.

Therefore, according to the current state of the art related to papain-pectin systems, the maximum obtained values for papain gels range from 600 to 1,800 U/mg (see Patent Application AR085779A1) and in the papain-propyleneglycol-polyethyleneglycol systems the maximum obtained values are approximately 600 U/mg (see WO2014016644A1).

Consequently, when evaluating the advantages and disadvantages of all the above mentioned systems, the conclusion is that it is advisable to have a papain-based enzymatic gel reformulated by improving the carrier means for this enzyme, one which is much more stable and has a greater power of action both on acute and chronic caries, one which also has a chronologically enhanced action, without the need for specific tools and avoiding use of potentially toxic products.

SUMMARY OF THE INVENTION

The present invention refers to a gel dental chemical composition for manual application, the objective of which is softening the carious dentin on the dental pieces for subsequent manual removal with tools, without resorting to the traditional methods with drills.

Therefore, the object of the present invention is a dental composition of papain in the form of a gel for the atraumatic treatment of caries which comprises papain having a final activity of at least 3,000 U/mg, wherein the papain is bio-encapsulated with a pH=7 buffer-$C_{3-6}$ polyol-pectin-$C_{2-6}$ alkanolamine-nonionic emulsifier mixture, together with pharmaceutically acceptable coloring agents, preservatives and solvents.

Preferably, the pH=7 buffer is selected from disodium or dipotassium acid phosphate ($Na_2HPO_4$, $K_2HPO_4$)/citric acid ($C_6H_8O_7$), sodium chloride (NaCl)/sodium citrate ($C_6H_5O_7Na_3.2H_2O$)/sodium hydroxide (NaOH), sodium or potassium diacid phosphate ($NaH_2PO_4$, $KH_2PO_4$)/disodium or dipotassium acid phosphate ($Na_2HPO_4$, $K_2HPO_4$), tris-(hydroxymethyl)-aminomethane (TRIS)/hydrochloric acid (HCl).

More preferably, pH=7 buffer is $KH_2PO_4$/$Na_2HPO_4$ buffer.

Preferably, pectin is apple bagasse pectin (core and peel) or citrus pectin.

More preferably, the pectin used is citrus pectin.

Also preferably, the $C_{3-6}$ polyol is selected from 1,2,3-propanetriol (glycerin), 1,2-propanediol (propyleneglycol), 1,3-butanediol, 1,4-butanediol, 1,3-butenediol, 2,3-butenediol, 2,2-dimethyl-1,3 propanediol (neopentylglycol), erythritol, sorbitol, mannitol, and mixtures thereof.

More preferably, the $C_{3-6}$ polyol is 1,2-propanediol (propyleneglycol).

Also preferably, the $C_{2-6}$ alkanolamine can be monoethanolamine, diethanolamine, triethanolamine, and mixtures thereof.

More preferably, the $C_{2-6}$ alkanolamine is triethanolamine.

Preferably, the non-ionic emulsifier is selected from the group consisting of: polyoxyethylene stearate 8 (E-430); polyoxyethylene stearate 40 (E-431); polyoxyethylene sorbitan monolaurate 20 (20 EO or ethoxylated with 20 oxyethylene units), also known as polysorbate 20 or Tween 20 (E-432); polyoxyethylene sorbitan monooleate 20, polysorbate 80 or Tween 80 (E-433); polyoxyethylene sorbitan monopalmitate 20, polysorbate 40 or Tween 40 (E-434); polyoxyethylene sorbitan monostearate 20, polysorbate 60 or Tween 60 (E-435); polyoxyethylene sorbitan tristearate 20, polysorbate 65 or Tween 65 (E-436); and mixtures thereof.

More preferably, the non-ionic emulsifier is polyoxyethylene sorbitan monooleate 20 (polysorbate 80 or Tween 80).

Additionally, the composition further contains a pharmaceutically acceptable coloring agent selected from methylene blue, toluidine blue, methyl green, methylene green, gentian violet, malachite green, methylene yellow, and mixtures thereof.

Preferably, the pharmaceutically acceptable coloring agent is toluidine blue.

Preferably, the preservative is selected from methylparaben, ethylparaben, propylparaben and mixtures thereof.

More preferably, the composition comprises papain (30,000 U/mg) 10.00% w/w, citrus pectin 8.00% w/w, propylene glycol 8.00% w/w, triethanolamine (99%) 0.72% w/w, TW80 (polyoxyethylene sorbitan monooleate 20 EO) 0.50% w/w, $KH_2PO_4$ 0.0378% w/w, $Na_2HPO_4$ 0.1283%, toluidine blue (1% w/w aq. sol.) 0.09% w/w, methylparaben 0.10% w/w, propylparaben 0.05% w/w, and distilled water 72.37% w/w.

A method of preparing the papain composition for the atraumatic treatment of caries described above is also proposed which comprises:

a) adding to distilled water while stirring at approximately 1,500 rpm the pH=7 buffer components, one or more pharmaceutically acceptable preservatives, and finally 30,000 U/mg papain until complete dispersion to neutral pH (pH=7);

b) moistening/wetting pectin while stirring in a $C_{3-6}$ polyol, then adding the non-ionic emulsifier, and finally a $C_{2-6}$ alkanolamine until neutralization of the pectin acidity thus forming a neutral encapsulating emulsion (pH=7); and c) adding the neutral encapsulating emulsion from step b) to the dispersion obtained in step a) under low speed stirring to obtain a buffer encapsulating emulsion (BEE), in the form of a stable gel of the papain dispersion.

Preferably, the described method comprises:

a) adding to distilled water while stirring at approximately 1,500 rpm potassium monobasic phosphate, sodium diacid phosphate, methylparaben, propylparaben, and finally 30,000 U/mg papain until complete dispersion to neutral pH (pH=7), thus obtaining a buffer dispersion;

b) moistening while stirring citrus pectin in propylene glycol by adding sorbitan monooleate, and finally triethanolamine until neutralization of the acidity of the citrus pectin thus forming a neutral encapsulating emulsion (pH=7); and c) adding the neutral encapsulating emulsion from step b) to the dispersion obtained in step a) under low speed stirring to obtain a buffer encapsulating emulsion (BEE), in the form of a stable gel of the papain dispersion.

Preferably, this method comprises the step of adding, while stirring, to the stable gel of the papain dispersion a coloring agent dissolved in a pharmaceutically acceptable solvent.

Preferably, the coloring agent is 1% w/w blue toluidine dissolved in distilled water.

Preferably, the stirring in step c) is performed between 20 and 150 rpm.

Preferably, the concentration ratio of citrus pectin/propylene glycol/triethanolamine ranges from 4/4/0.36 to 10/10/0.90, expressed in % w/w, respectively.

Most preferably, the concentration ratio of citrus pectin/propylene glycol/triethanolamine is 8/8/0.72, expressed in % w/w.

Additionally, the method comprises the step of packing the obtained gel in multi-dose syringes.

DETAILED DESCRIPTION OF THE INVENTION

Figure 1:
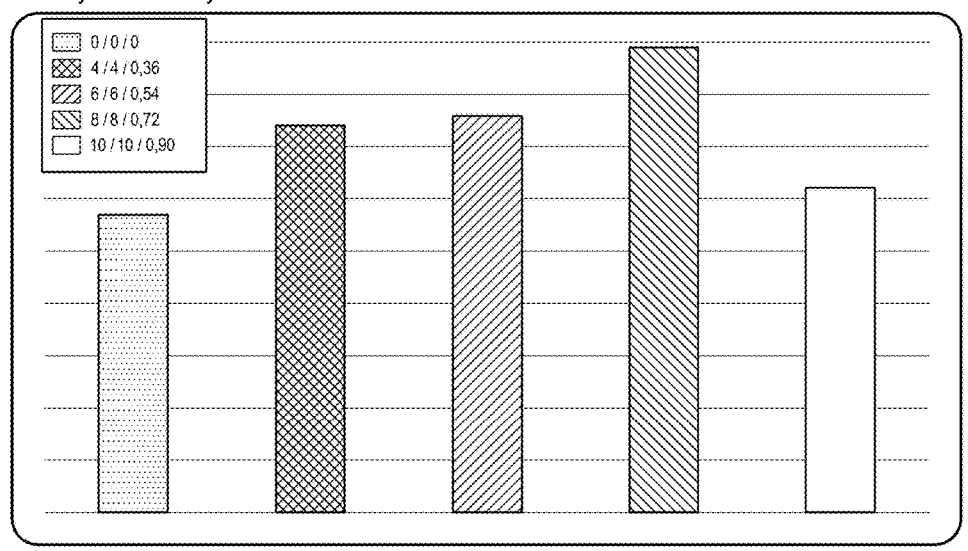
FIG. 1 shows a chart of the activity of the immobilized papain enzyme in the buffer encapsulating emulsion at different concentration ratios of citrus pectin/propylene glycol/triethanolamine according to Example 2.

Therefore, in order to solve the prior art issues, a papain topical gel composition is proposed for dental use, which is recommended for the removal of dead carious dentin tissue in dental pieces.

Thus, the gel presented herein is based on papain as the sole component which differs from the already known products because its active principle, the papain enzyme, is in the form of a dispersion with an active content of at least 3,000 U/mg and it is occluded in a buffer encapsulating emulsion (BEE) as the encapsulating, wetting and stabilizing agent, which immobilizes and confers stability; this exponentially increases the enzymatic activity of the final product during the storage time.

Consequently, a greater proteolytic effectiveness is achieved to remove the collagen fibers of the carious tissue; the active principle is less dissolved by to the oral fluids, a greater resistance to storage is achieved even under unfavorable conditions with no need of refrigeration, and also a greater antibacterial and antifungal power with increased antiseptic power at the tissue level. Furthermore, this gel does not contain chloramine in its formula, which enhances its toxicological safety features.

The active agent is papain, a vegetable protease, which is used to remove the necrotic tissue from skin lesions in the presence of some encapsulating agent, such as a biopolymer, which makes it stable.

Pectin is a polysaccharide, a high molecular weight macromolecule, which is one of the main components of the cell walls of plants, responsible for the characteristic texture of plants. Pectins are widely used in the food, pharmaceutical and cosmetic industries, mainly as thickening and stabilizing agents.

According to the present invention, compositions with values of at least 3,000 U/mg have been obtained, which greatly exceed the levels achieved in the art so far.

In order to attain this unexpected result, the work was based on a bio-encapsulation papain system by dispersing it in a system consisting of pH=7 buffer-$C_{3-6}$ polyol-pectin-$C_{2-6}$ alkanolamine-non-ionic emulsifier.

A preferred embodiment of the present invention is a dental papain composition in the form of a gel for the atraumatic treatment of caries which comprises papain with a final activity of at least 3,000 U/mg, wherein the papain is bio-encapsulated in a pH=7 buffer-$C_{3-6}$ polyol-pectin-$C_{2-6}$ alkanolamine-nonionic emulsifier mixture, together with pharmaceutically acceptable coloring agents, preservatives and solvents.

According to the present invention, the pectin employed to bio-encapsulate the papain may be pectin from apple bagasse (core and peel) or citrus pectin. More preferably, citrus pectin is used for the gel composition of the present invention.

Preferably, the pH=7 buffer is selected from disodium or dipotassium acid phosphate ($Na_2HPO_4$, $K_2HPO_4$)/citric acid ($C_6H_8O_7$), sodium chloride (NaCl)/sodium citrate ($C_6H_5O_7Na_3.2H_2O$)/sodium hydroxide (NaOH), sodium or potassium diacid phosphate ($NaH_2PO_4$, $KH_2PO_4$)/disodium or dipotassium acid phosphate ($Na_2HPO_4$, $K_2HPO_4$), and tris-(hydroxymethyl)-aminomethane (TRIS)/hydrochloric acid (HCl).

The pH=7 buffer employed in the composition of the invention is the potassium diacid phosphate ($KH_2PO_4$)/disodium acid phosphate ($Na_2HPO_4$) buffer.

Furthermore, also preferably, the $C_{3-6}$ polyol used in the dental composition of the invention is 1,2,3-propanetriol (glycerin), 1,2-propanediol (propyleneglycol), 1,3-butanediol, 1,4-butanediol, 1,3-butenediol, 2,3-butenediol, 2,2-dimethyl-1,3-propanediol (neopentylglycol), erythritol, sorbitol, mannitol.

More preferably, the employed $C_{3-6}$ polyol is 1,2-propanediol (propyleneglycol).

Propyleneglycol, or propane-1,2-diol, is an organic compound, an alcohol, or, to be more specific, a diol, which is colorless, odorless and tasteless. It is a clear, viscous liquid, which is hygroscopic and miscible with water, acetone and chloroform. It is obtained by hydration of propylene oxide.

The American Food and Drug Administration (FDA) has determined that propyleneglycol is Generally Recognized as Safe (GRAS) for use in food, cosmetics and medicine. Propyleneglycol metabolizes to lactic acid, a reaction which naturally occurs in the working muscles.

By using this compound, the gel remains stable even if its container is open without getting dry or obstructing the syringe applicator.

On the other hand, the $C_{2-6}$ alkanolamine used in the composition according with the present invention to neutralize the acid pH can be monoethanolamine, diethanolamine or triethanolamine. Preferably, the $C_{2-6}$ alkanolamine used is triethanolamine.

Triethanolamine is an organic compound mainly composed of a tertiary amine and three hydroxyl groups with the general chemical formula $C_6H_{15}NO_3$. Like other amines, triethanolamine functions as a weak chemical base due to the electronic pair available on the nitrogen atom.

It appears as a viscous liquid although it may be solid when impure, depending on the temperature; it is clear, pale yellow to colorless, not very hygroscopic and volatile, completely soluble in water and miscible with most oxygen-containing organic solvents. It has a slight ammonia odor.

This chemical is used for pH adjustment in cosmetic, hygiene and cleaning preparations. Among the cosmetic and hygiene products we may include skin lotions, eye gels, moisturizers, shampoos, shaving foams, etc.

A non-ionic emulsifier is also used in a preferred embodiment of the composition of the invention, which is selected from the group consisting of: polyoxyethylene stearate 8 (E-430); polyoxyethylene stearate 40 (E-431); polyoxyethylene sorbitan monolaurate 20 (20 EO or ethoxylated with 20 oxyethylene groups) (also known as polysorbate 20, Tween 20 or E-432); polyoxyethylene sorbitan monooleate 20 (polysorbate 80, Tween 80 or E-433); polyoxyethylene sorbitan monopalmitate 20 (polysorbate 40, Tween 40 or E-434); polyoxyethylene sorbitan monostearate 20 (polysorbate 60, Tween 60 or E-435); polyoxyethylene sorbitan tristearate 20 (polysorbate 65, Tween 65 or E-436); and mixtures thereof.

Particularly, according to a preferred embodiment of the composition of the invention, polyoxyethylene sorbitan monooleate 20 (Tween 80) is used as the non-ionic emulsifier.

It is an additive used in the food industry which acts as a non-ionic lipophilic detergent emulsifying and dissolving fat. It has been approved by the European Community for use in Food and it is identified as Emulsifier 433 (E-433).

The composition according to the invention further comprises a pharmaceutically acceptable coloring agent.

Said pharmaceutically acceptable coloring agent is selected from methyl blue, toluidine blue, methyl green, methylene green, gentian violet, malachite green, methylene yellow, and mixtures thereof.

Particularly, the pharmaceutically acceptable coloring agent used in the composition of the invention is toluidine blue.

Toluidine blue is a coloring agent which also acts as a powerful antimicrobial agent by fixing itself to the bacterial wall, being a non-toxic photosensitizing agent because most oral bacteria do not absorb visible light.

Finally, the preservative used in the gel composition is selected from the group consisting of methylparaben, ethylparaben, propylparaben and mixtures thereof. Preferably, in a preferred embodiment of the composition, a combination of methylparaben and propylparaben is used.

A preferred embodiment of the composition comprises papain (30,000 U/mg) 10.00% w/w, citrus pectin 8.00% w/w, propyleneglycol 8.00% w/w, triethanolamine (99%) 0.72% w/w, polyoxyethylene sorbitan monooleate 20 EO (Tween 80) 0.50% w/w, $KH_2PO_4$. 0.0378% w/w, $Na_2HPO_4$ 0.1283%, toluidine blue (1% w/w aq. sol.) 0.09% w/w, methylparaben 0.10% w/w, propylparaben 0.05% w/w, and distilled water 72.37% w/w.

The secondary ingredients used are also used in the food industry, which grants toxicology safety.

It is another object of the present invention to provide a method of preparing the papain composition for the atraumatic treatment of caries as described above, which comprises:

a) adding to distilled water while stirring at approximately 1,500 rpm the components of a pH=7 buffer, one or more pharmaceutically acceptable preservatives, and finally 30,000 U/mg papain until complete dispersion to a final neutral pH (pH=7);

b) wetting pectin while stirring in a $C_{3-6}$ polyol, then adding the non-ionic emulsifier, and finally a $C_{2-6}$ alkanolamine until neutralization of the pectin acidity thus forming a neutral encapsulating emulsion (pH=7); and c) adding the neutral encapsulating emulsion from step b) to the dispersion obtained in step a) under low speed stirring to obtain a buffer encapsulating emulsion (BEE), in the form of a stable gel of the papain dispersion.

The described method preferably comprises:

a) adding to distilled water while stirring at approximately 1,500 rpm potassium monobasic phosphate, sodium diacid phosphate, methylparaben, propylparaben, and finally 30,000 U/mg papain until complete dispersion to a final neutral pH (pH=7);

b) wetting while stirring citrus pectin in Propyleneglycol, adding sorbitan monooleate, and finally triethanolamine until neutralization of the citrus pectin thus forming a neutral encapsulating emulsion (pH=7); and c) adding the neutral encapsulating emulsion from step b) to the dispersion obtained in step a) under low speed stirring to obtain a buffer encapsulating emulsion (BEE), in the form of a stable gel of the papain dispersion.

The method further comprises the step of adding, while stirring, to the stable gel of the papain dispersion a pharmaceutically acceptable coloring agent dissolved in a pharmaceutically acceptable solvent.

Preferably, the coloring is 1% w/w blue toluidine dissolved in distilled water.

Preferably, the stirring in step a) is performed at approximately 1,500 rpm, and the stirring in step c) is performed between approximately 20 and approximately 150 rpm.

More preferably, the concentration ratio of citrus pectin:propyleneglycol:triethanolamine employed in the method ranges from 4:4:0.36 to 10:10:0.90 expressed in % w/w, respectively.

Still more preferably, the concentration ratio of citrus pectin:propyleneglycol:triethanolamine is 8:8:0.72 expressed in % w/w. In this system, the papain shows greater activity Once the desired dental composition is obtained, it is analyzed to verify it is in proper condition to be fractionated. For this purpose, the method comprises the step of packing the obtained gel into multi-dose syringes.

In this way, the gel is packed into multi-dose syringes, for example, 1.0-ml syringes. The secondary packing is performed in cardboard boxes, each containing a syringe with its corresponding sticker and package insert. These boxes are closed with a sealing wafer so that the container is properly sealed.

EXAMPLES

Example 1

Manufacturing of the Composition of the Invention

In a 316 stainless steel reactor equipped with a lower dispersing disc and a W-shaped blade for gel stirring, which are independently operated by means of a double shaft and an engine to stir the formula of this encapsulating system.

The total amount of distilled water is added into the reactor with the dispersing system spinning at 1,500 rpm; then the monobasic potassium phosphate and the sodium diacid phosphate are added; then, methyl paraben and propyl parabeno; and finally the 30,000 U/mg papain is added until complete dispersion.

Unlike other compositions, a papain dispersion in a pH=7 buffer solution is obtained instead of a solution in distilled water without any pH control over time, which is essential for enzymatic stability; a non-aqueous papain solution in polyethyleneglycol is not obtained either, which is a product that would react with strong oxidizing agents. As examples for the latter, the products resulting from chloramine T decomposition can be mentioned, as this compound is used in some compositions as a preservative, considering that if inhaled, it may cause cough, chest pain, nose irritation and sore throat. It is a flammable, hazardous raw material.

If the disperser were stopped, most of the enzyme would precipitate, so stirring is maintained and the next emulsion is added which is prepared in an independent 316 stainless steel vessel in which citrus pectin is wetted in propyleneglycol, polyoxythelene sorbitan monooleate 20 EO (Tween 80) is added, which is an excellent wetting surfactant that significantly improves the wetting and penetration power of the gel in the dental cavities, thus increasing the application efficacy of the final product. Then triethanolamine is added to neutralize the acidity of the citrus pectin thus forming a neutral emulsion (pH=7), therefore the pH will not be modified when it is added to the previously described papain dispersion.

When adding the neutral encapsulating emulsion to the papain dispersion the W-shaped blade is turned on at approximately 150 rpm thus obtaining a stable gel from the papain dispersion. Once it is homogenous, the gel is ready to be fractionated.

Example 2

Selection of the Papain Concentration in Citrus Pectin:Propyleneglycol:Triethanolamine 1 g of citrus pectin is wetted and the formed emulsion is easily solubilized in distilled water. It is concluded that 1 g of citrus pectin is well wetted from 1 g of propyleneglycol. Then 0.09 g of triethanolamine is added to achieve pH=7. Therefore, the mass ratio for citrus pectin:propyleneglycol:triethanolamine is 1:1:0.09 in % w/w, respectively. Different solutions were prepared by varying the concentration of citrus pectin:propyleneglycol:triethanolamine while keeping the above developed ratio, namely: 4:4:0.36; 6:6:0.54; 8:8:0.72; 10:10:0.90 in % w/w, respectively, using distilled water as the solvent.

A final 10% p/v concentration of papain enzyme was added to the solutions. In order to assess the effect of the different concentrations of citrus pectin:propyleneglycol:triethanolamine on the enzyme, the enzymatic activity expressed by the papain was estimated through the Kunitz spectrophotometric method (1946). Said method employs a reaction mixture composed of 2 ml 0.1 M buffer phosphate, pH=6; 1 mL 1% casein (substrate) and 1 ml of enzymatic extract sample (papain in citrus pectin:propyleneglycol:triethanolamine); the mixture is incubated for 30 minutes at 37° C., when this period is over the reaction is quenched with 20% trichloroacetic acid and it is allowed to stand for 20 minutes. To separate the enzymatic hydrolysis products, the mixture was centrifuged at 3,500 rpm for 30 minutes in an AWEL MF 20 Nuaire instrument.

Finally, the supernatant was separated and the peptide absorbance equivalent to 1 µg of released tyrosine per minute was obtained at 280 nm in a T60-UV PG Instruments UV-VIS Spectrophotometer (190-1100 nm) having a 2 nm bandwidth. A 0.005 ml µg$^{-1}$ cm$^{-1}$ molar extinction coefficient was used.

The obtained results are shown in FIG. 1, where it can be seen that the immobilized papain enzyme in the neutral encapsulating emulsion increased its activity by 30% with respect to the free enzyme and, without intending to be tied to any theory, this result seems to indicate that the support somehow worked on the enzyme active conformation.

By using the concentration ratio 8:8:0.72 expressed in % w/w for the neutral encapsulating emulsion, an activity increase greater than 55% was obtained as compared to the enzyme in solution (see FIG. 1); this was the greatest value observed, and for this reason, that ratio was selected for the formulation of the composition according to the present invention as it showed the greatest activity. Higher concentrations showed decreased activity, even close to the free enzyme activity and, again, without intending to be tied to any theory, this may be due to steric hindrance of the active site of the enzyme and low diffusion rate of the substrate.

0.5% polyoxythelene sorbitan monooleate 20 EO is added to the selected encapsulating emulsion before neutralization with triethanolamine in order to increase its wetting power, then the papain dispersion prepared according to Example 1 and the coloring agent are also added, thus obtaining a preferred embodiment of the gel composition according to the present invention:

| Component | Composition |
|---|---|
| Papain (30,000 U.I/mg) | 10.00 g |
| Citrus pectin | 8.00 g |
| Propyleneglycol | 8.00 g |
| 99% Triethanolamine | 0.723 g |
| TW80 (polyoxyethylene sorbitan monooleate 20 EO) | 0.50 g |
| $KH_2PO_4$ | 0.0378 g |
| $Na_2HPO_4$ | 0.1283 g |
| 1% w/w toluidine blue in distilled water | 0.09 g |
| Methylparaben | 0.10 g |
| Propylparaben | 0.05 g |
| Distilled water | 72.37 g |

Example 3

Effectiveness Comparison Between a State-of-the-art Composition and the Composition of the Present Invention A comparative study between papain gels was conducted, namely Papacaries Duo (gel A) versus the composition of Example 2 (gel B).

To that end, the clinical efficacy was assessed by comparing Papacaries Duo to the composition according to the present invention; the following parameters were evaluated: treatment time, degree of pain (Chipps scale), caries detector, required time in the mouth without total isolation, room temperature drying and the operator's support of gels A and B for subjective efficacy in general performance. Statistically, the superior clinical efficacy of the composition of the present invention (gel B) over its prior art counterpart (gel A) is proved.

The present investigation was performed with randomly selected patients. These were 30 patients aged 6 to 17, plus 10 adults aged 35 to 70, who were the former's parents, all of them presenting dental caries, with no pulpitis or irreversible damage. Thus, an overall 40-patient sample was obtained.

50% of the selected patients underwent a chemo-mechanical treatment with Papacaries Duo, whereas the rest of the group was treated with the composition of the invention in order to assess: efficacy in caries removal, signs of pain, operative times and behavior with the caries detector.

Material and Methodology Description.

The employed method comprises chemical removal followed by mechanical removal using manual tools, and subsequent application of the caries detector to have clear evidence of the state of the injury. The final filling is performed with a glass ionomer cement.

The following compositions were used: Papacaries Duo (gel A) and the composition of the invention prepared according to the above Example 2 (gel B).

A Densell caries detector was employed in both applications.

The dentists who performed the operations were provided with two syringes only labelled A and B, with no other identification.

The results were returned in the form of a Table where the following was indicated: treatment time (minutes), degree of pain (Chipps scale), caries detector (+, −), required time (minutes) in the mouth without total isolation, room temperature drying (+, −), and the operator's support (gel A or gel B) for subjective efficacy in general performance.

Result Analysis.

Figure 2:
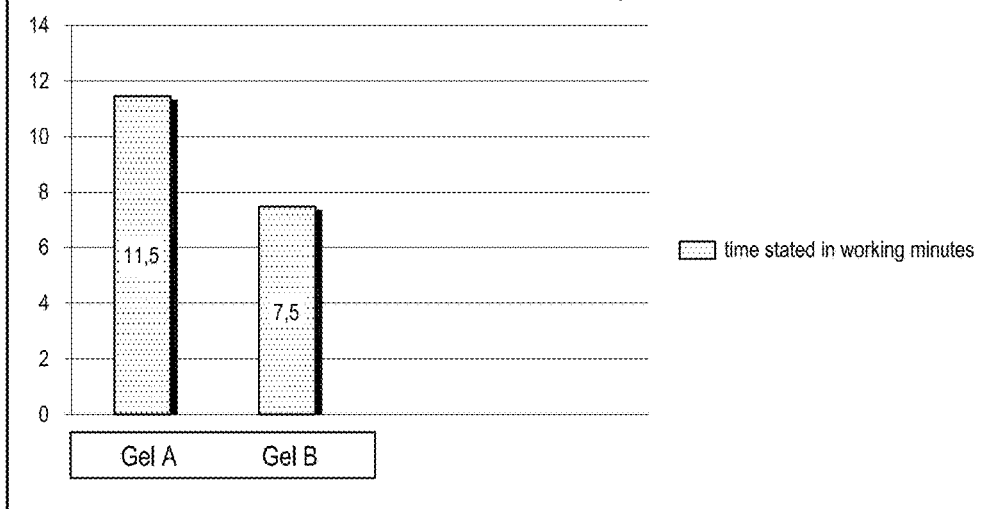
FIG. 2 shows a comparative chart of the time stated in working minutes in the oral cavity for Gels A and B in Example 3.

It was determined that the composition according to the present invention (gel B) needed shorter working times in the mouth (see FIG. 2), approximately 7.5 minutes on average.

Figure 3A:
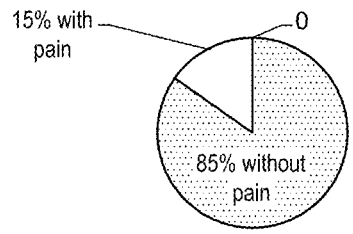
FIGS. 3 A and 3 B show pie charts of the result distribution of the degree of pain according to the Chipps scale for Gels A and B, respectively.
Figure 3B:
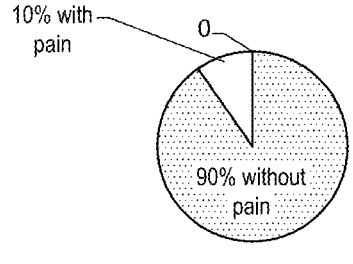

As regards the degree of pain, both behaved similarly without showing statistically significant differences, with a small 5% advantage for the composition of the present invention (see FIGS. 3 A and 3 B).

Figure 4A:
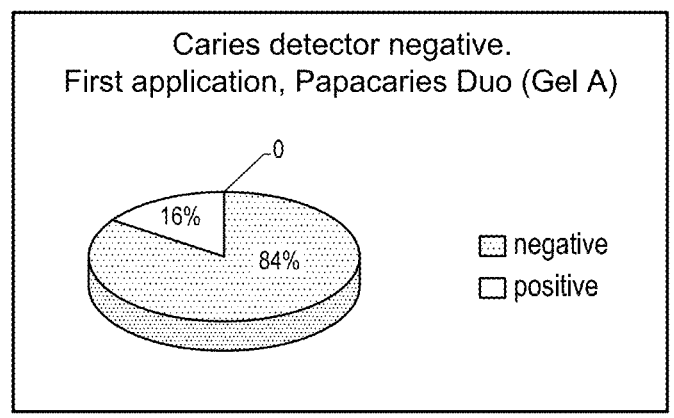
FIGS. 4 A and 4 B show pie charts of the result distribution for exposure to the caries detector after the first application for Gels A and B, respectively.
Figure 4B:
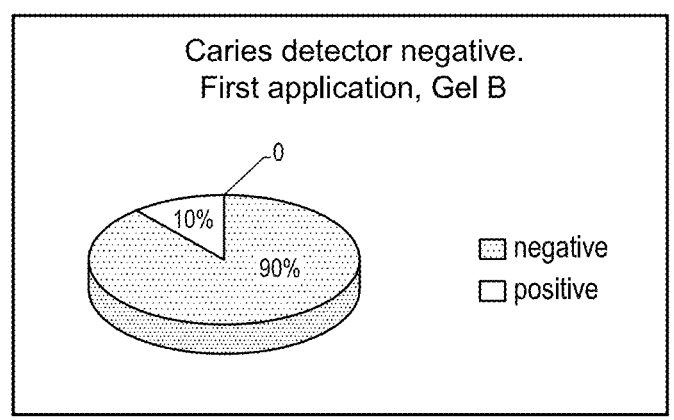
Figure 5A:
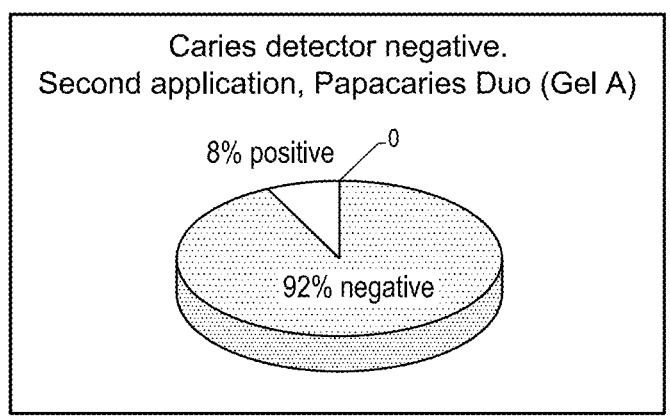
FIGS. 5 A and 5 B show pie charts of the result distribution for exposure to the caries detector after the second application for Gels A and B, respectively.
Figure 5B:
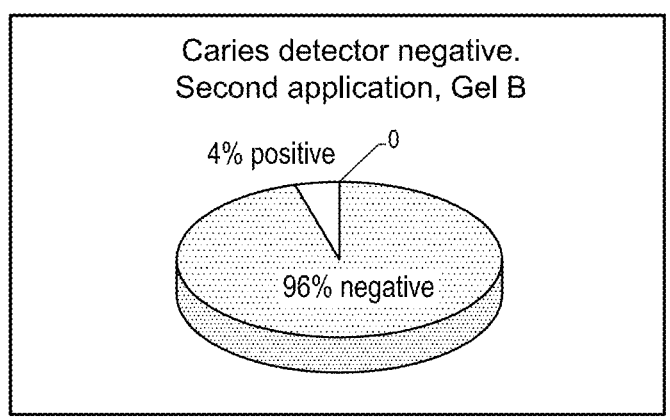

As concerns exposure to the caries detector, the composition of the invention showed greater efficiency in its first application (90% negative), while Papacaries Duo achieved the same level of efficiency at its second application (92% negative). See FIGS. 4 A and 4 B for the first application and FIGS. 5 A and B for the second application.

The composition of the invention stays, on average, 1 additional minute in the oral cavity of patients without total isolation. The reaction to drying is similar for both compositions (10 for Papacaries Duo, 8 for the present composition).

Subjective efficacy, measured by the operator, is as follows: 70% of the intervening dentists in the trials preferred the composition of the present invention as the working material while 30% preferred Papacaries Duo.

None of the patients showed inflammatory reactions in the tissues surrounding the treatment area with either product.

Conclusions.

It can be concluded that, even when both products fulfill the stated objective as regards removal of the necrotic tissue, it can be clinically observed that the composition of the invention has an advantage over Papacaries Duo which is directly attributable due to the components and the way the dental composition is prepared.

Example 4

Verification of Stability and Enzymatic Activity of the Gel Dental Composition Check as Regards Temperature Samples of a composition manufactured according to the method described in the present invention were taken with the objective of analyzing the residual enzymatic activity at different temperatures: room temperature and a higher temperature selected as the maximum temperature which the composition might be exposed to during storage at room temperature in summer.

| Property | Sample (25° C.) | Sample (36° C.) |
|---|---|---|
| Enzymatic activity (papain) | 3,350 U/mg | 3,550 U/mg |
| pH | 7.0 | 7.0 |
| Density | 1.45 g/cm$^3$ | 1.45 g/cm$^3$ |
| Viscosity | >100,000 mPa/s | >100,000 mPa/s |

One Sample (25° C.) was analyzed at a room temperature of 25° C. and the other Sample (36° C.) was analyzed at 36° C. after a storage period of 48 hours at that temperature; the results for both samples are shown in the above Table.

The enzymatic activity, far from decreasing, increased approximately by 5.6%. Therefore, it can be concluded that the composition of the present invention is acceptably stable as to be marketed and used without the need to be kept under cooling conditions.

APPLICATION EXAMPLES

The present Application Examples were performed by means of an atraumatic restoring technique; this procedure is based on excavating and removing decay from tooth using only manual tools and then filling it with the appropriate material. The following cases have all been treated with said technique using the composition according to the present invention. The results which are shown have been obtained from patients of different ages and dentists with minimum technical training in order to show the efficacy of the composition of the present invention.

Each application of the composition comprises a period of approximately 1.5 minutes, during which time the gel is in contact with the dental piece, with relative isolation with cotton rolls, no use of rotary tools and without using local anesthesia.

Application Example 1

Figure 6:
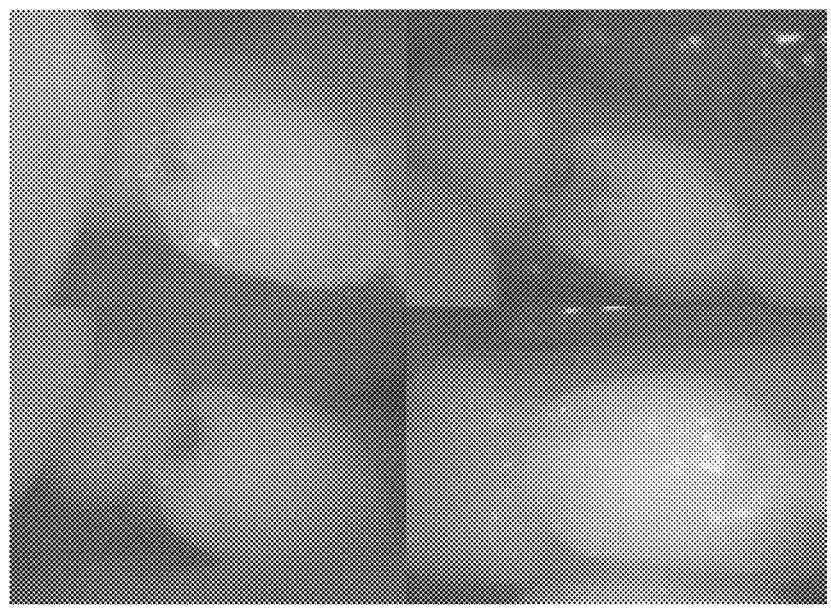
FIG. 6 shows a series of photographs corresponding to the Application Example 1.

Seven-year-old patient. Treatment of piece 85 with one application of the composition. Total working time: 11 minutes. The caries detector was applied. See the treatment sequence from left to right in FIG. 6.

Application Example 2

Figure 7:
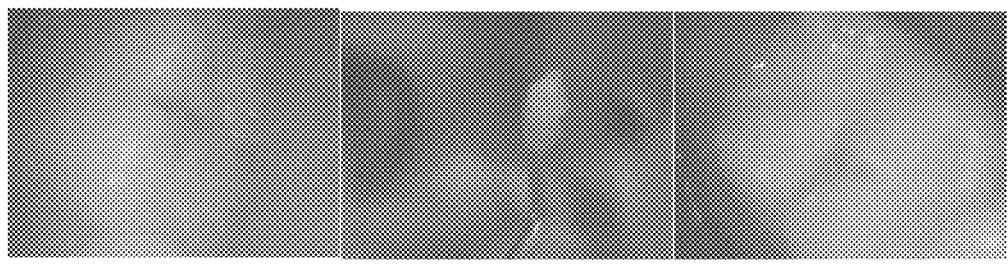
FIG. 7 show a series of photographs corresponding to Application Example 2.

Seven-year-old patient. Treatment of piece 46 with three applications of the composition. No use of turbine or anesthesia. Total working time: 7 minutes. See FIG. 7, where the second photograph (on the right) shows the proteolysis product removed with a spoon.

Application Example 3

Figure 8:
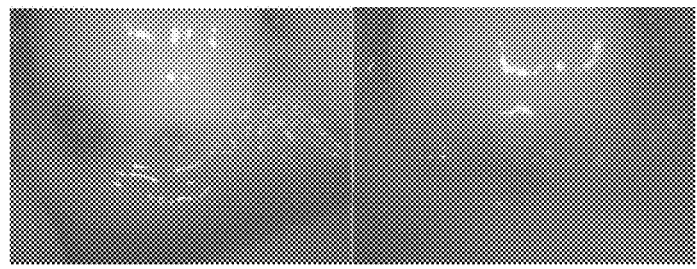
FIG. 8 shows a series of photographs corresponding to the Application Example 3.

Forty-five-year-old patient. Treatment of piece 46 with two applications of the composition. Dental piece with caries in the neck, without using rotary tools or anesthesia; use of relative isolation. Total working time: 10 minutes. See FIG. 8, where the second photograph (on the right) shows the healthy condition of the soft tissues after treatment.

Application Example 4

Figure 9:
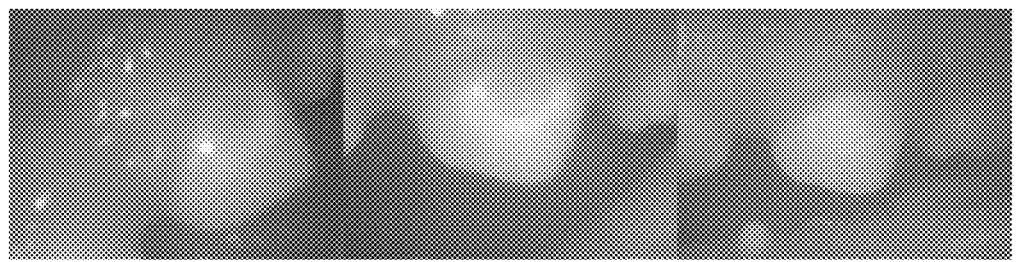
FIG. 9 shows a series of photographs corresponding to the Application Example 4.

Seven-year-old phobic patient. Treatment of piece 65 with two applications of the composition. Dental piece with caries in the vestibular surface, filling IV type 2. Total working time: 6 minutes See the treatment sequence from left to right in FIG. 9.

Application Example 5

Figure 10:
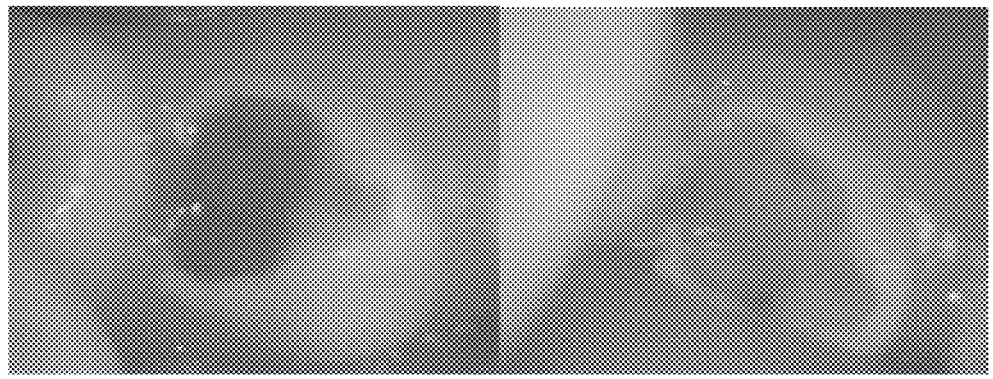
FIG. 10 shows a series of photographs corresponding to Application Example 5.

Seven-year-old patient undergoing their first dental treatment. Treatment of piece 65 with two applications of the composition. Isolation with cotton rolls. Total working time: 8 minutes. See FIG. 10, where the second photograph shows residual affected dentin with a possibility of remineralization.

Application Example 6

Figure 11:
FIG. 11 shows a series of photographs corresponding to Application Example 6.

Thirty-five-year-old patient with bruxism and a neck caries. Treatment of piece 13 with three applications of the composition. Total working time: 5 minutes. See FIG. 11.

Application Example 7

Figure 12:
FIG. 12 shows a series of photographs corresponding to Application Example 7.

Eight-year-old patient. Treatment of piece 53 with three applications of the composition. Total working time: 6 minutes. See FIG. 12.

Application Example 8

Figure 13:
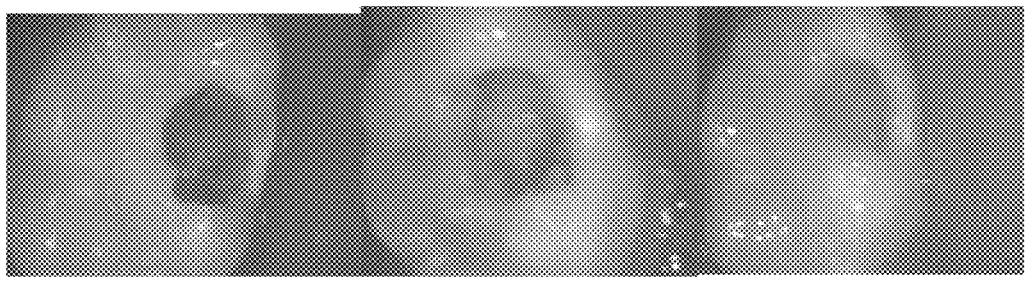
FIG. 13 shows a series of photographs corresponding to Application Example 8.

Extremely phobic, twenty-eight-year-old patient; the first time to undergo a filling procedure. Treatment of piece 36 with three applications of the composition. No rotary tools or anesthesia were used. Retentive cavity, dental tissue economy, rough surface after treatment which improved adhesion. Total working time: 11 minutes. See FIG. 13.

Application Example 9

Figure 14:
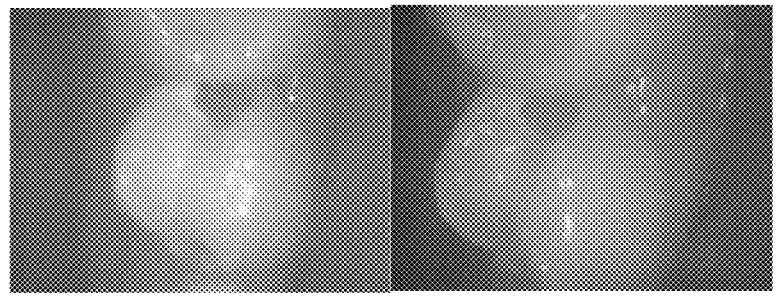
FIG. 14 shows a series of photographs corresponding to Application Example 9.

Six-year-old patient undergoing their first dental treatment experience. Treatment of piece 64 with one application of the composition. Total working time: 5 minutes. See FIG. 14.

Application Example 10

Figure 15:
FIG. 15 shows a series of photographs corresponding to Application Example 10.

Fourteen-year-old adolescent patient with fast spreading caries. Treatment of piece 36 with two applications of the composition. Total working time: 12 minutes. See FIG. 15.

Application Example 11

Figure 16:
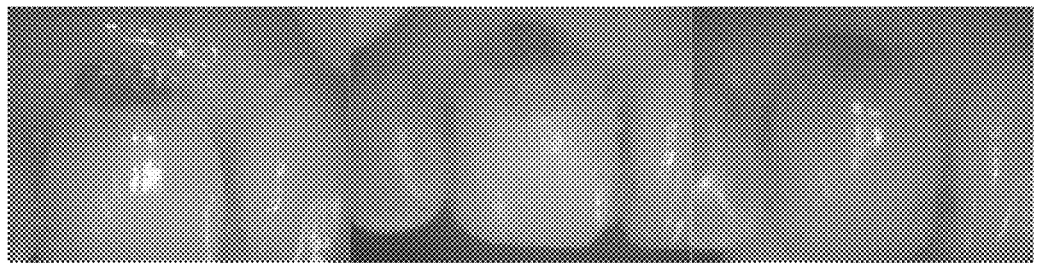
FIG. 16 shows a series of photographs corresponding to Application Example 11.

Forty-eight-year-old patient. Treatment of piece 11 with three applications of the composition. Granule removal. Total working time: 11 minutes. See FIG. 16.

Application Example 12

Figure 17:
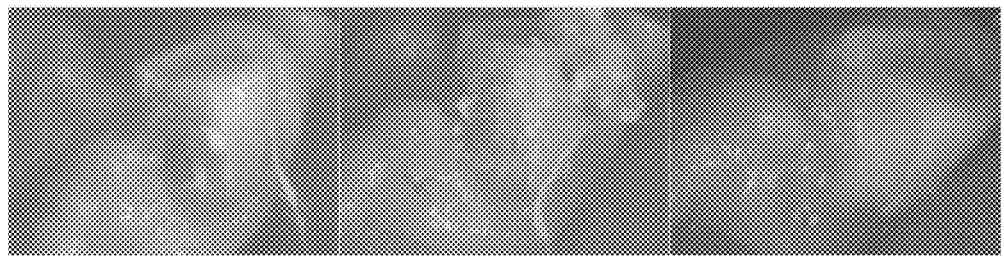
FIG. 17 shows a series of photographs corresponding to Application Example 12.

Eighty-year-old patient. Treatment of piece 43 with three applications of the composition. Thread removal. Total working time: 13 minutes. See FIG. 17.

Application Example 13

Figure 18:
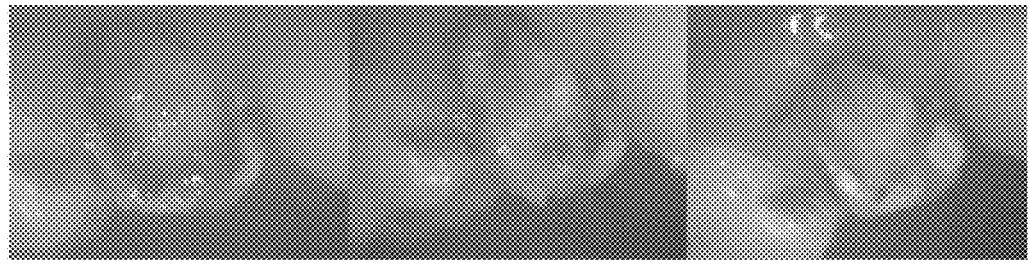
FIG. 18 shows a series of photographs corresponding to Application Example 13.

Twenty-seven-year-old patient. Treatment of piece 23 with two applications of the composition. Total working time: 10 minutes. See FIG. 18.

Application Example 14

Figure 19:
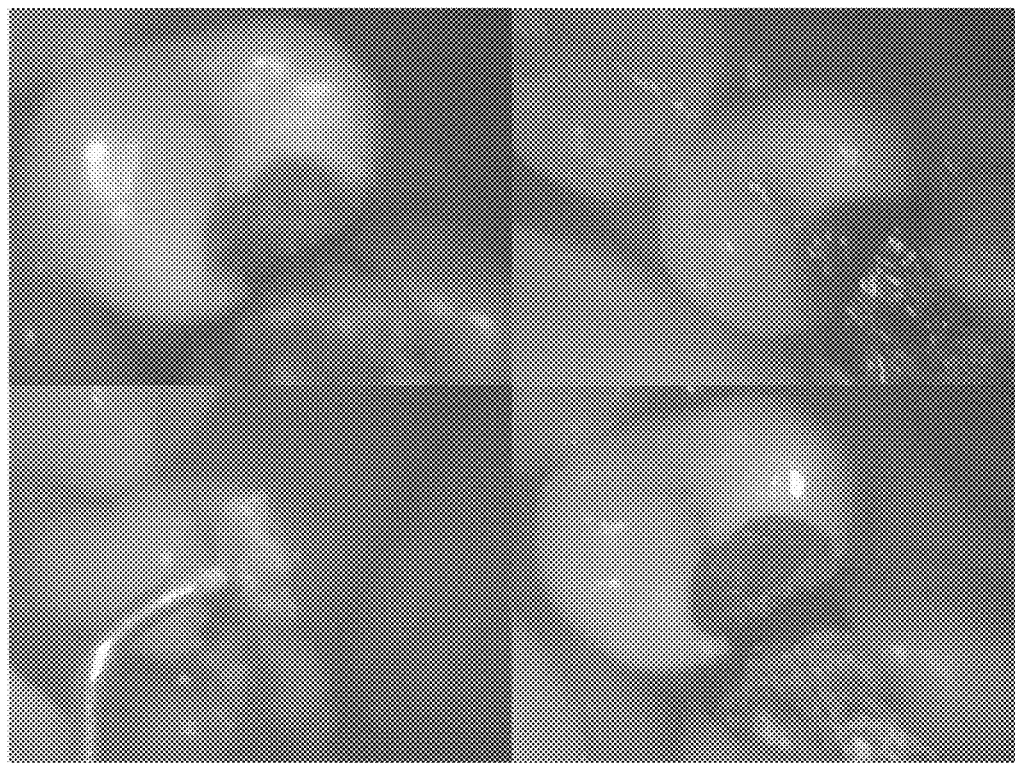
FIG. 19 shows a series of photographs corresponding to Application Example 14.

Fifty-six-year-old patient. Treatment of piece 25 with three applications of the composition. Monoblock removal. Total working time: 12 minutes. See FIG. 19.

Application Example 15

Figure 20:
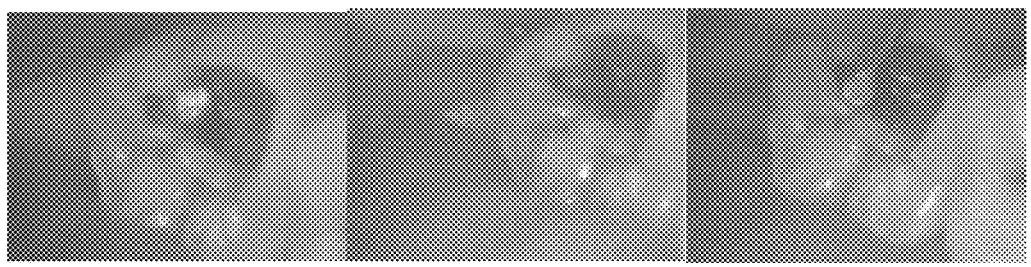
FIG. 20 shows a series of photographs corresponding to Application Example 15.

Twenty-nine-year-old patient. Treatment of piece 47 with three applications of the composition. Amalgam infiltrated with carious injury, pigmented regions of dentin, application of caries detector. Total working time: 12 minutes. See FIG. 20.

The invention claimed is:

1. A dental composition of papain in the form of a gel for the atraumatic treatment of caries comprising papain with a final activity of at least 3,000 U/mg, wherein the papain is bio-encapsulated in a mixture comprising all of the following ingredients:
   pH=7 buffer,
   a $C_{3-6}$ polyol,
   pectin,
   $C_{2-6}$ alkanolamine,
   a nonionic emulsifier,
   optionally a pharmaceutically acceptable coloring agent
   a preservative, and
   a solvent,
   wherein the composition does not include chloramine.

2. The composition according to claim 1, wherein the pH=7 buffer is selected from the group consisting of: disodium or dipotassium acid phosphate ($Na_2HPO_4$, $K_2HPO_4$)/citric acid ($C_6H_8O_7$), sodium chloride (NaCl)/sodium citrate ($C_6H_5O_7Na_3$. $2H_2O$)/sodium hydroxide (NaOH), sodium or potassium diacid phosphate ($NaH_2PO_4$, $KH_2PO_4$)/disodium or dipotassium acid phosphate ($Na_2HPO_4$, $K_2HPO_4$), tris-(hydroxymethyl)-aminomethane (TRIS)/hydrochloric acid (HCl).

3. The composition according to claim 1, wherein the pH=7 buffer is $KH_2PO4/Na_2HPO_4$.

4. The composition according to claim 1, wherein the $C_{3-6}$ polyol is selected from the group consisting of: 1,2,3-propanetriol (glycerin), 1,2-propanediol (propyleneglycol), 1,3-butanediol, 1,4-butanediol, 1,3-butenediol, 2,3-butenediol, 2,2-dimethyl-1,3 propanediol (neopentylglycol), erythritol, sorbitol, mannitol, and mixtures thereof.

5. The composition according to claim 4, wherein the $C_{3-6}$ polyol is 1,2-propanediol (propyleneglycol).

6. The composition according to claim 1, wherein the pectin is apple bagasse pectin or citrus pectin.

7. The composition according to claim 6, wherein the pectin employed is citrus pectin.

8. The composition according to claim 1, wherein the $C_{2-6}$ alkanolamine is selected from the group consisting of: monoethanolamine, diethanolamine, triethanolamine and mixtures thereof.

9. The composition according to claim 8, wherein the $C_{2-6}$ alkanolamine is triethanolamine.

10. The composition according to claim 1, wherein the non-ionic emulsifier is selected from the group consisting of: polyoxyethylene stearate 8; polyoxyethylene stearate 40; polyoxyethylene sorbitan monolaurate 20; polyoxyethylene sorbitan monooleate 20; polyoxyethylene sorbitan monopalmitate 20; polyoxyethylene sorbitan monostearate 20; polyoxyethylene sorbitan tristearate 20; and mixtures thereof.

11. The corn position according to claim 10, wherein the non-ionic emulsifier is polyoxyethylene sorbitan monooleate 20.

12. The composition according to claim 1, wherein the pharmaceutically acceptable coloring agent is present and is selected from the group consisting of: methyl blue, toluidine blue, methyl green, methylene green, gentian violet, malachite green, methylene yellow, and mixtures thereof.

13. The composition according to claim 12, wherein the pharmaceutically acceptable coloring agent is toluidine blue.

14. The composition according to claim 12, wherein the preservative is selected from the group consisting of: methylparaben, ethylparaben, propylparaben and mixtures thereof.

15. The composition according to claim 14, wherein the preservative is the mixture of methylparaben and propylparaben.

16. A dental composition of papain in the form of a gel for the atraumatic treatment of caries, said composition comprising papain 10.00% w/w, citrus pectin 8.00% w/w, propyleneglycol 8.00% w/w, triethanolamine 0.72% w/w, polyoxyethylene-20 sorbitan monooleate 0.50% w/w, $KH_2PO_4$ 0.0378% w/w, $Na_2HPO_4$ 0.1283%, toluidine blue (1% w/w aq. sol.) 0.09% w/w, methylparaben 0.10% w/w, propylparaben 0.05% w/w, and distilled water 72.37% w/w,
   wherein the composition has a final activity of papain of at least 3000 U/mq, and
   wherein the composition does not include chloramine.

17. A method of preparing the papain dental composition of claim 1 for the atraumatic treatment of caries, said method comprising:
   a) adding to distilled water while stirring at approximately 1,500 rpm the components of a pH=7 buffer, one or more pharmaceutically acceptable preservatives, and finally 30,000 U/mg papain until complete dispersion to a final neutral pH (pH=7);
   b) wetting pectin while stirring in a $C_{3-6}$ polyol, then adding the non-ionic emulsifier, and finally a $C_{2-6}$ alkanolamine until neutralization of the pectin acidity thus forming a neutral encapsulating emulsion (pH=7); and
   c) adding the neutral encapsulating emulsion from step b) to the dispersion obtained in step a) under low speed stirring to obtain a stable gel comprising papain.

18. The method according to claim 17, said method comprising a further step of adding under stirring, to the stable gel comprising papain, a coloring agent dissolved in a pharmaceutically acceptable solvent.

19. The method according to claim 17, wherein the stirring in step c) is performed at between approximately 20 and approximately 150 rpm.

20. The method according to claim 17, wherein the concentration ratio of pectin/$C_{3-6}$ polyol/$C_{2-6}$ alkanolamine employed ranges from 4/4/0.36 to 10/10/0.90 expressed in % w/w, respectively.

21. The method according to claim 20, wherein the concentration ratio of pectin/$C_{3-6}$ polyol/$C_{2-6}$alkanolamine is 8/8/0.72 expressed in % w/w.

22. The method according to claim 17, said method further comprising the step of packing the obtained gel into multi-dose syringes.

23. A method of preparing the papain dental composition of claim 1 for the atraumatic treatment of caries, said method comprising:
   a) adding to distilled water while stirring at approximately 1,500 rpm potassium monobasic phosphate, sodium diacid phosphate, methylparaben, propylparaben, and finally 30,000 U/mg papain until complete dispersion to a final neutral pH (pH=7);
   b) wetting while stirring citrus pectin in propyleneglycol, adding polyoxyethylene sorbitan monooleate 20 , and finally triethanolamine until neutralization of the citrus pectin thus forming a neutral encapsulating emulsion (pH=7), wherein the concentration ratio of citrus pectin/propyleneglycol/triethanolamine employed ranges from 4/4/0.36 to 10/10/0.90 expressed in % w/w, respectively;

c) adding the neutral encapsulating emulsion from step b) to the dispersion obtained in step a) under low speed stirring between approximately 20 and approximately 150 rpm to obtain a stable gel of papain dispersion;

d) adding under stirring to the stable gel of papain toluidine blue as coloring agent dissolved in a pharmaceutically acceptable solvent; and e) packing the obtained gel into multi-dose syringes.

24. The method according to claim 23, wherein the toluidine blue coloring agent is added as a solution of 1% w/w toluidine blue dissolved in distilled water.

* * * * *

UNITED STATES PATENT AND TRADEMARK OFFICE
CERTIFICATE OF CORRECTION

PATENT NO. : 10,137,178 B2
APPLICATION NO. : 15/312431
DATED : November 27, 2018
INVENTOR(S) : Mauricio Dobboletta Page 1 of 1

It is certified that error appears in the above-identified patent and that said Letters Patent is hereby corrected as shown below:

On the Title Page

Item (56), under "Foreign Patent Documents," the date of the cited reference WO 20050290946 A1 should read -- 03/2005 -- rather than "10/2013".

In the Claims

At Column 15, Claim number 11, Line number 58, "corn position" should read -- composition --.

At Column 16, Claim number 16, Line number 17, "U/mq" should read -- U/mg --.

Signed and Sealed this
Ninth Day of July, 2019

Andrei Iancu
*Director of the United States Patent and Trademark Office*